US010768162B2

(12) United States Patent
Sutton (10) Patent No.: US 10,768,162 B2
(45) Date of Patent: Sep. 8, 2020

(54) SYSTEMS AND METHODS FOR PRODUCING AGRICULTURAL PRESCRIPTIONS

(71) Applicant: AirScout Inc., Lowell, IN (US)

(72) Inventor: Brian Harold Sutton, Lowell, IN (US)

(73) Assignee: Airscout Inc., Lowell, IN (US)

( * ) Notice: Subject to any disclaimer, the term of this patent is extended or adjusted under 35 U.S.C. 154(b) by 233 days.

(21) Appl. No.: 15/923,774

(22) Filed: Mar. 16, 2018

(65) Prior Publication Data
US 2018/0267008 A1 Sep. 20, 2018

Related U.S. Application Data

(60) Provisional application No. 62/472,137, filed on Mar. 16, 2017.

(51) Int. Cl.
| | | |
|---|---|---|
| G01N 33/24 | (2006.01) | |
| G06K 9/00 | (2006.01) | |
| G01N 25/56 | (2006.01) | |
| G06T 7/70 | (2017.01) | |
| G06T 7/00 | (2017.01) | |
| G06T 11/60 | (2006.01) | |

(52) U.S. Cl.
CPC .......... *G01N 33/246* (2013.01); *G01N 25/56* (2013.01); *G01N 33/24* (2013.01); *G06K 9/00657* (2013.01); *G06T 7/0016* (2013.01); *G06T 7/70* (2017.01); *G01N 2033/245* (2013.01); *G06K 2009/00644* (2013.01); *G06T 11/60* (2013.01); *G06T 2207/10016* (2013.01); *G06T 2207/10032* (2013.01); *G06T 2207/10048* (2013.01); *G06T 2207/30188* (2013.01)

(58) Field of Classification Search
CPC ...... G01N 33/246; G01N 25/56; G01N 33/24; G01N 2033/245; G06T 7/0016; G06T 7/70; G06T 2207/10016; G06T 2207/10048; G06T 2207/30188; G06T 2207/10032; G06T 11/60; G06K 9/00657; G06K 2009/00644
See application file for complete search history.

(56) References Cited

U.S. PATENT DOCUMENTS

| | | | |
|---|---|---|---|
| 2018/0020622 A1* | 1/2018 | Richt | G06F 16/00 703/6 |
| 2018/0075545 A1* | 3/2018 | Richt | G06Q 10/063 |

* cited by examiner

*Primary Examiner* — Bobbak Safaipour
(74) *Attorney, Agent, or Firm* — Hartman Global IP Law; Gary M. Hartman; Domenica N. S. Hartman (57) ABSTRACT

Methods and systems suitable for producing agricultural prescriptions and/or measuring or monitoring parameters that are used in the production of the prescriptions. According to one aspect, such a method includes obtaining and recording a series of aerial thermal images of a field over a period of time, and analyzing the series of aerial thermal images to determine nutrient mineralization rates for the field.

20 Claims, 7 Drawing Sheets
(7 of 7 Drawing Sheet(s) Filed in Color)

Wet,Cool     FIG. 1a     Dark Area (Wet,Cool)

Dry, Warm     FIG. 1b     Dark Area (Dry,Warm)

FIG. 8

SYSTEMS AND METHODS FOR PRODUCING AGRICULTURAL PRESCRIPTIONS

CROSS REFERENCE TO RELATED APPLICATIONS

This application claims the benefit of U.S. Provisional Application No. 62/472,137, filed Mar. 16, 2017, the contents of which are incorporated herein by reference.

BACKGROUND OF THE INVENTION

The present invention generally relates to methods of producing agricultural prescription maps (referred to as prescriptions). More particularly, this invention relates to aerial imaging of agricultural fields and plants growing therein to determine nutrient availability in the soil and plant nutrient requirements of the plants during growth.

The term "agricultural prescription" generally refers to planting rates, fertilizer rates (e.g., nitrogen, foliar feeds), etc. that may be recommended for various locations within a given agriculture (crop) field following an assessment of conditions within the field so that growing conditions can be optimized to promote crop production. Basic parameters for building a precise agricultural prescription for a field include locations (e.g., identifying locations in the field for planting, fertilization, etc.) and quantities (e.g., identifying the amounts of fertilizer to be applied). While various methods exist for determining quantities in general, it is believed that the location parameter is often neglected. For example, SSURGO soil maps (soil survey maps available from the National Resources Conservation Service) and yield history may provide generalized, incomplete, and/or unreliable information. Reliance on such information to produce prescriptions may yield inaccurate or less than optimal results.

Using fertilization prescriptions as an example, throughout many years of testing and prior history, the ability to determine nitrogen contents and mineralization rates of various soil types within a given field has been very elusive and time consuming. There are numerous existing methods intended to determine available nitrogen content in a soil sample, but little or no reliable methods for determining where the sample should be taken in a field. This commonly requires that soil samples are taken in random locations of the field with poor results.

In view of the above, it can be appreciated that there is an ongoing desire to improve the accuracy of agricultural prescriptions, and that it would be particularly desirable if systems and methods were available for identifying specific locations within a field for testing and/or monitoring parameters that can be used in the production of the prescriptions.

BRIEF DESCRIPTION OF THE INVENTION

The present invention provides methods and systems suitable for producing agricultural prescriptions and/or measuring or monitoring parameters that are used in the production of the prescriptions.

According to one aspect of the invention, a method is provided that includes obtaining and recording a series of aerial thermal images of a field over a period of time, and analyzing the series of aerial thermal images to determine nutrient mineralization rates for the field.

Another aspect of the method described above includes the steps of obtaining and recording a series of aerial visual spectrum images of the field over the period of time, analyzing the aerial thermal images and the aerial visual spectrum images to predict a yield estimate for the field, determining a total amount of a nutrient required by plants in the field during the growing season based on the yield estimate, and then producing a nutrient prescription by at least subtracting the amount of the nutrient naturally provided to the field via nutrient mineralization from the total amount of the nutrient required by the plants.

According to another aspect of the invention, a method is provided that includes obtaining and recording a series of aerial thermal images of a field over a period of time, and analyzing the series of aerial thermal images to monitor water infiltration rates and soil hydrology of the field following rain events.

According to another aspect of the invention, a method is provided that includes obtaining and recording a series of aerial thermal images of a field over a period of time, and analyzing the series of aerial thermal images to determine location placement of soil probes to determine mineralization of a nutrient in the field, uptake of the nutrient by plants in the field, availability of the nutrient in the field, and an amount of the nutrient required by the plants during growth.

According to another aspect of the invention, a method is provided that includes obtaining and recording a series of aerial thermal images of a field over a period of time, and analyzing the series of aerial thermal images to determine locations for soil testing to determine mineralization of a nutrient in the field, uptake of the nutrient by plants in the field, availability of the nutrient in the field, and an amount of the nutrient required by the plants during growth.

Other aspects of the invention include systems configured to perform the steps of one or more of the methods described above.

Technical effects of the methods and systems described above preferably include the capability of improving the accuracy of agricultural prescriptions by identifying specific locations within a field for testing and/or monitoring parameters that are used in the production of the prescriptions.

Other aspects and advantages of this invention will be further appreciated from the following detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

This disclosure provides systems and methods which utilize aerial thermal imagery for the purpose of deriving agricultural prescriptions, particularly with the intent of improving agricultural prescriptions. The aerial thermal imagery may be performed using thermal imaging systems and methods of the types disclosed in U.S. Patent Application Publication No. 2016/0216245 to Sutton (hereinafter referred to as Sutton), the entire contents of which are incorporated herein by reference. Such systems and methods may improve the accuracy of, for example, nutrient prescriptions and thereby reduce fertilization costs, as well as reduce fertilizer-related pollution, for example, into water supplies.

For convenience, the following disclosure will focus primarily on the nitrogen contents of soils and nitrogen-containing nutrient (fertilization) prescriptions. However, it will be understood that the methods, systems, and concepts described herein may be used to improve the accuracy of various types of agricultural prescriptions relating to various other plant nutrients and are relevant to agricultural activities in general. Nonlimiting examples of other nutrients that the invention may be applicable to include phosphorus, potassium, calcium, magnesium, sulfur, copper, iron, manganese, molybdenum, zinc, boron, silicon, cobalt, vanadium, and various rare mineral catalysts. Further, aspects of the invention will be described in relation to crops grown in agricultural fields of farms. However, it is within the scope of the invention that the methods, systems, and concepts described herein are applicable to crops and other plants grown in other (e.g., nonagricultural) environments.

In reference to a nutrient prescriptions concerning nitrogen, a nitrogen-containing fertilization prescription for a field is based, at least in part, on the amount of naturally available nitrogen in the soil and the amount of nitrogen required by the plants during the growth season to achieve a desired yield. Nitrogen soil levels ordinarily depend in part on mineralization, which is a process by which microbes decompose nitrogen-containing organic matter (e.g., manure, crop residues, etc.) to ammonium. Because it is a biological process, mineralization rates typically vary with soil temperature, moisture content, and aeration. The present invention utilizes measured soil-related and water-related characteristics of various regions of a field whose soil and water contents may widely vary. This approach may include identifying soil types and organic matter content (e.g., decomposing plant or animal material in the soil) from which various different soil zones in the field may be designated that can affect nutrient mineralization. Although various methods and systems are available for determining this information, current thermal and Advanced Digital Vegetation Index (ADVI) systems are particular well suited for obtaining high resolution aerial thermal and visual spectrum images of the bare soil of a field, as disclosed in Sutton. For example, aerial thermal and visual (e.g., visual spectrum) images may be obtained of the bare soil (i.e., little or no vegetation, for example, prior to the planting or emergence of a crop) of a field. From the visual image, an ADVI image may be produced and then compared to the thermal image to determine various different types of soil present in the field and the locations of the different soil types, for example based on contrast (e.g., color and/or brightness) between various areas of the field. Preferably, the thermal image is used to compensate for moisture in the field which can reduce light reflectance and be erroneously mistaken for areas of darker soil. By analyzing the two types of images, a soil zone map may be produced accurately indicating boundaries or zones based on the colors and light intensity captured within a field.

Figure 1A:
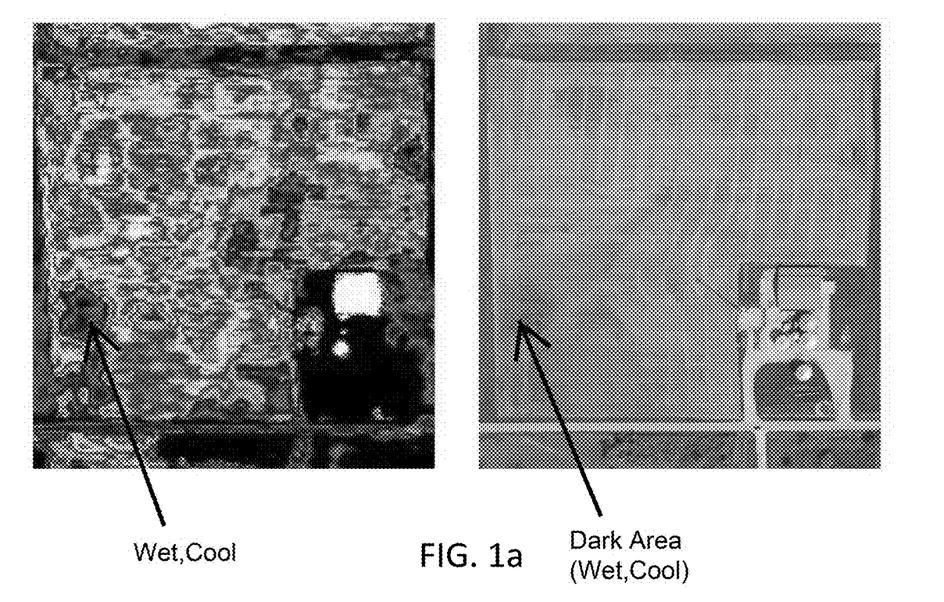
FIGS. 1a and 1b each contain an aerial thermal image obtained of the same field that were obtained at different times prior to the planting or emergence of a crop in the field, with each aerial thermal image being individually paired with a visual spectrum image of the field that was obtained at the same time as the thermal image with which it is paired for the purpose of identifying soil types while compensating for soil moisture content in accordance with a nonlimiting aspect of the invention.
Figure 1B:
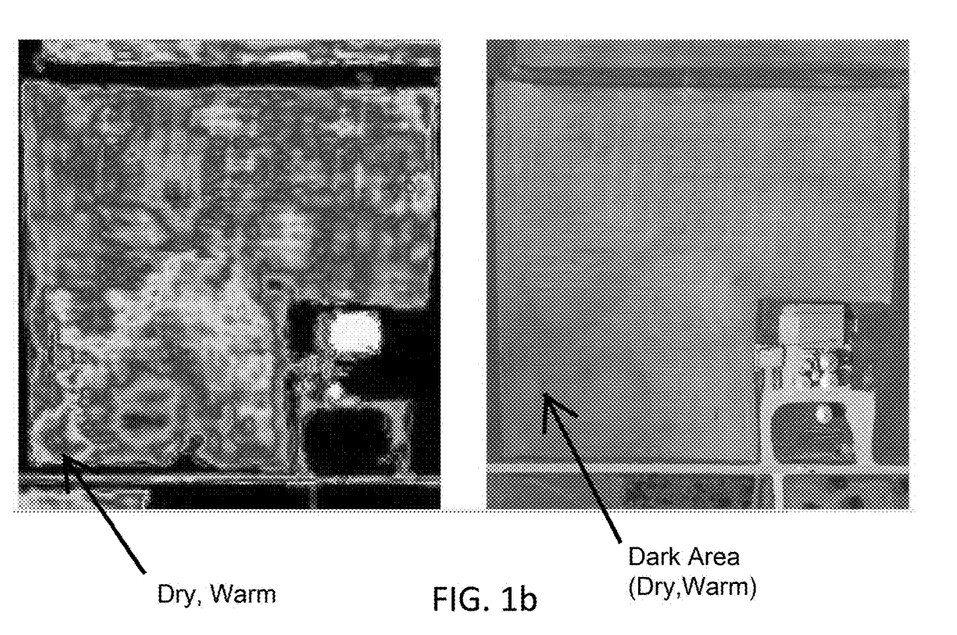

As a nonlimiting example, FIGS. 1a and 1b contain two pairs of thermal and visual images of the same field, but with the images of FIG. 1a acquired at a different time than the images of FIG. 1b. The pair of images in FIG. 1a were obtained when the field was relatively wet (e.g., during or after a rain or irrigation event), and the pair of images in FIG. 1b were obtained when the field was drier. In general, if a field is dry, darker colored soils tend to be relatively warmer than surrounding lighter colored soils since the darker colored soils absorb heat while lighter colored soils reflect heat due to their respective colors. Therefore, areas of a field that are dark in color in the visual image (righthand images of FIGS. 1a and 1b) and cool (purple) in the thermal image (left-hand images of FIGS. 1a and 1b) are likely wet on the surface, such as the field location identified in FIG. 1a. Conversely, if a dark area in the visual image of a field is warm (red) in the thermal image, it is likely dry on the surface, such as the field location identified in FIG. 1b.

Figure 2A:
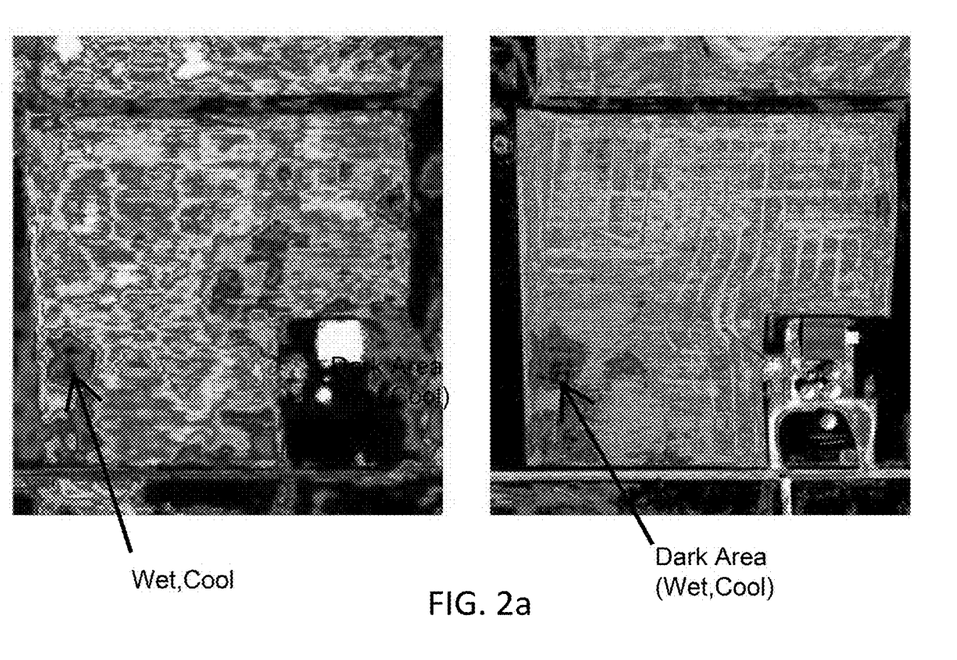
FIGS. 2a and 2b contain the pair of aerial thermal images of FIGS. 1a and 1b, respectively, each of which is individually paired with an Advanced Digital Vegetation Index (ADVI) image of the field that was obtained at the same time as the thermal image with which it is paired for the purpose of identifying soil types while compensating for soil moisture content in accordance with a nonlimiting aspect of the invention.
Figure 2B:
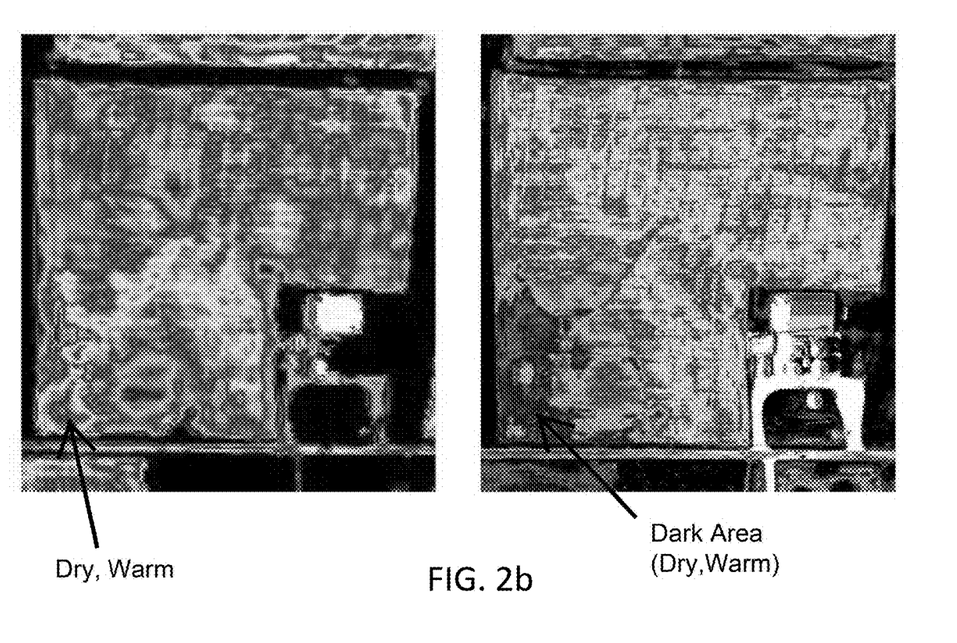

FIGS. 2a and 2b represent the same thermal images of FIGS. 1a and 1b paired with ADVI images of the same field. The dark areas of the field are more clearly identified in the ADVI images (purple) than in the visual images of FIGS. 1a and 1b. The color and temperature of the soil may now be compared by comparing corresponding pixels between the thermal and ADVI images. In this instance, the pair of images in FIG. 2a identify the indicated area of the field as both cool and dark (purple in both images) signifying that the area is wet. In contrast, the indicated area of the field in the pair of images in FIG. 2b is identified as warm (red) in the thermal image, but dark (purple) in the ADVI image, signifying that the area is dry.

In addition to or as an alternative to the above-noted thermal/ADVI soil identification methods, soil types may be identified using conventional methods, for example, that include physical testing of soil samples from the field. Nonlimiting examples of soil testing equipment are disclosed in U.S. Patent Application Publication No. 2016/0270289 to Schildroth et al., the contents of which are incorporated herein by reference. While not intending to promote any particular interpretation, it appears that soil testing equipment such as those disclosed in Schildroth et al. are capable of identifying a variety of soil properties that may be useful in preparing nutrient prescriptions. However, it is believed that these types of systems are limited in their reliance on testing a plurality of soil samples from a field, which may be burdensome to the farmer and potentially produce less accurate results. Therefore, according to nonlimiting aspects of the invention, it is believed that soil testing methods and systems similar to those disclosed in Schildroth et al. may be improved by using aerial thermal and/or ADVI imagery to identify specific locations for soil testing and/or soil probe placement. Such locations may be based on, for example, data relating to water infiltration, water holding capacity, drainage rates, compaction issues, soil type (e.g., identifying regions of different soil types with thermal/ADVI system even if exact types have not yet been determined), organic matter content, crop yield predictions, and nutrient uptake within areas the field. As described herein and/or in Sutton, these data may be determined using the thermal and/or ADVI imagery. By considering this information, specific locations for soil testing and/or soil probe placement may be determined to improve testing results and/or reduce the number of tests and/or probes required for a field.

A field under consideration may be analyzed to determine various water-related properties, nonlimiting examples of which include water holding characteristics, water infiltration rates, and hydrologic drainage rates either of the previously identified soil zones or of identified water zones, which can affect nutrient mineralization. This is preferably accomplished using aerial thermal imagery either alone or in conjunction with soil moisture and temperature probes placed in the field as disclosed in Sutton. For example, aerial thermal images of the field may be obtained during or after rain and/or irrigation events to determine how each area of the field reacts to, for example, various rain intensities, quantities, and/or frequencies. For example, a soil moisture probe may be used to monitor moisture in an area of the field and the recorded moisture data can be compared to an aerial thermal image of the field (for example, assigned to one or more pixels in the thermal image corresponding to the location of the probe). Temperature differences between the pixels corresponding to the probe's location and the other pixels in the thermal image can be analyzed to determine the moisture content of each pixel in the field. In particular, the relativity among the pixels in the thermal image can be used to determine areas of the field that are wetter (cooler) than the location of the probe, and areas that are dryer (hotter). By monitoring moisture of the field with the probe and a series of thermal images, for example, prior to, during, and after a rain event, relative moisture changes within the field can be analyzed to identify movement of water from the rainfall over the field, as well as water holding, infiltration, and drainage rates for various areas of the field.

Figure 3A:
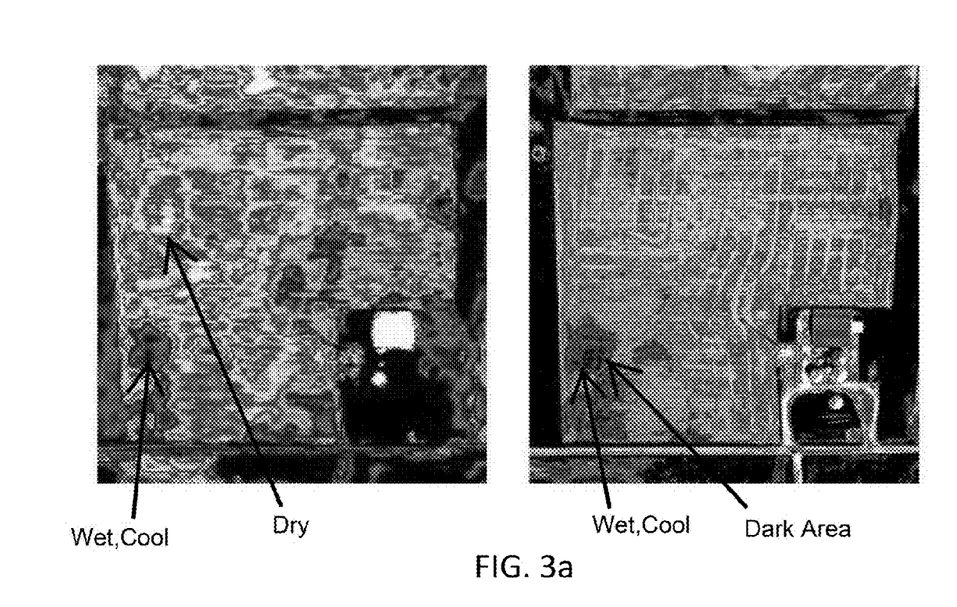
FIGS. 3a and 3b contain the pairs of images of FIGS. 2a and 2b, respectively, with dry and wet spots identified in the aerial thermal images of the field for the purpose of identifying locations for the placement of moisture probes in accordance with a nonlimiting aspect of the invention.
Figure 3B:
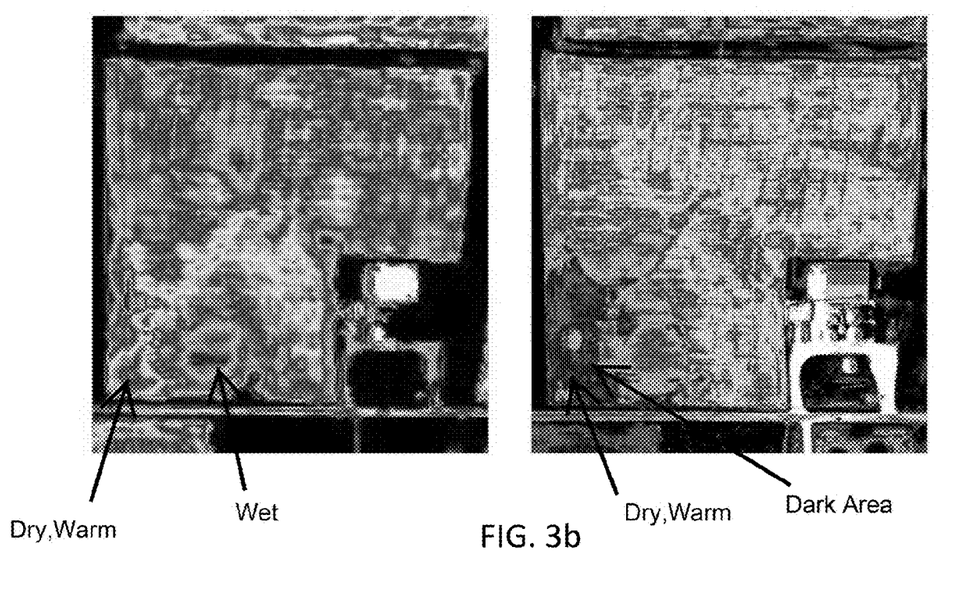

Preferably, the above process is performed with a soil moisture probe located in at least a relatively wet (ideally the wettest) area and a relatively dry (ideally the driest) area of the field to provide an accurate range of moisture. Such locations may be determined by comparing thermal and ADVI images of the field. For example, FIGS. 3a and 3b contain the pairs of thermal and ADVI images of FIGS. 1a and 2a and FIGS. 2a and 2b, respectively, which as noted previously were acquired of the same field at different times, with the field being relatively wet in FIG. 3a and relatively drier in FIG. 3b. In order to identify the driest area of the field to place a moisture probe, the pair of images in FIG. 3a may be analyzed to find a dry spot (i.e., warm and light colored) while the field is generally wet. In order to identify the wettest area of the field to place a moisture probe, the pair of images in FIG. 3b may be analyzed to find a wet spot (i.e., cool and dark colored) when the field is generally dry. Although the wet and dry areas of the field may fluctuate with various rain or irrigation events, this procedure can provide relatively wet and dry spots in the field for placement of moisture probes. Optionally, this procedure can be used to place moisture probes and/or other types of probes to provide additional information, such as mineral or nutrient content (e.g., nitrate or phosphorous levels), pH level, salinity, etc.

Figure 4:
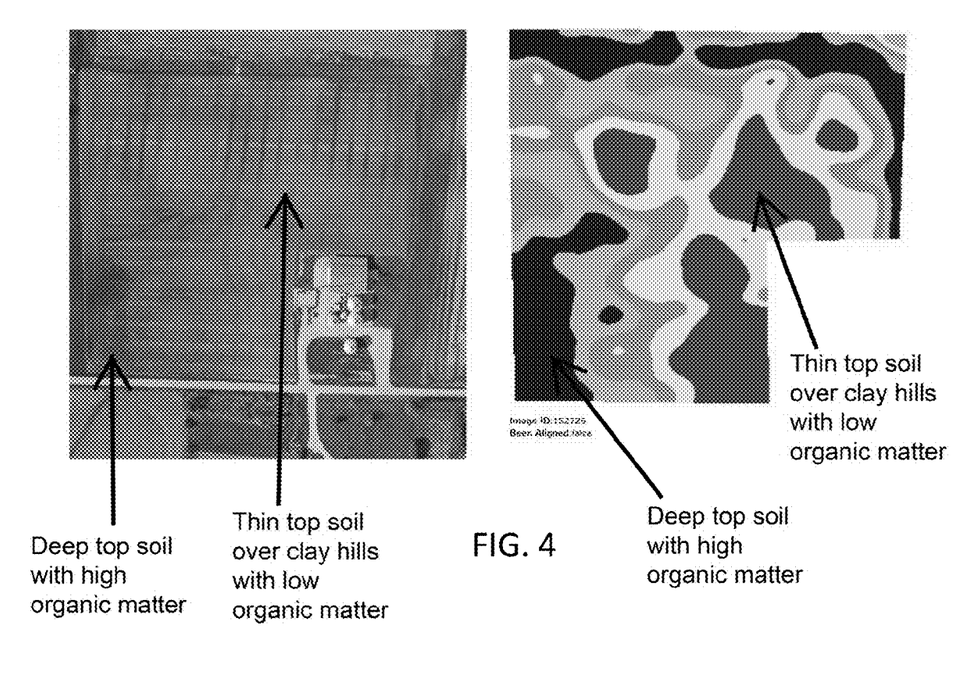
FIG. 4 contains an aerial visual spectrum image and an ADVI image of the field seen in FIG. 1 (obtained on a different day than FIGS. 1 through 3) for the purpose of identifying organic matter content within the soil in accordance with a nonlimiting aspect of the invention.
Figure 5A:
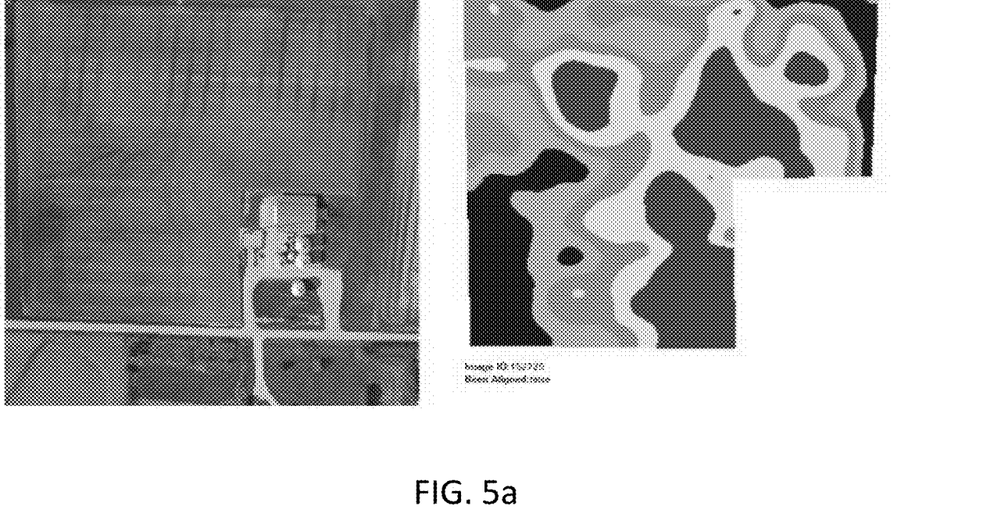
FIG. 5a contains the aerial visual spectrum and ADVI images of FIG. 4 aerial visual spectrum, ADVI, and FIG. 5b contains two thermal images of the same field obtained on different days for the purpose of monitoring moisture and temperature of the field in accordance with a nonlimiting aspect of the invention.
Figure 5B:
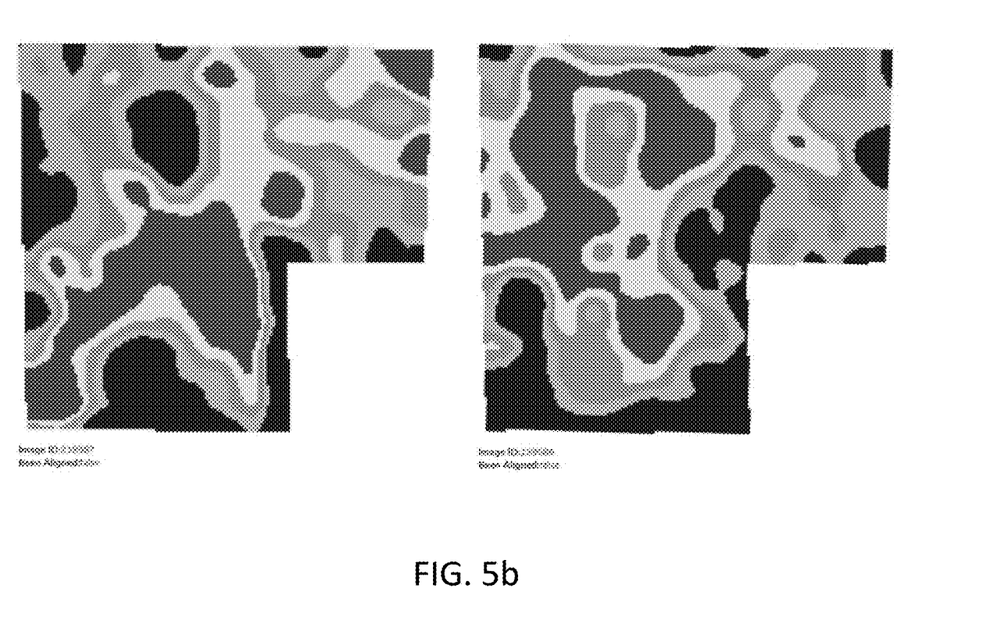

Based on the collected soil-related and water-related data, models can be produced to predict, for example, nitrogen mineralization rates and naturally available nitrogen content by soil zone as indicated by the thermal and ADVI images of FIGS. 1a through 3b. For example, the collected data may be used to produce a model to identify, for example, aerobic and anaerobic areas within the field, and predict microbial enzyme activity in the soil. As a nonlimiting example, FIG. 4 represents a pair of visual spectrum and ADVI images of the same field depicted in FIGS. 1a through 3b. These images may be analyzed to identify organic matter concentrations within the soil based on the color of the bare soil. In order to determine whether changes in color indicate a change in soil type or a change in organic matter concentration, the collected water-related data may be analyzed. For example, different soil types generally allow water to infiltrate differently, which can be observed via thermal imagery after a rain and/or irrigation event. Therefore, analyzing both the color of the bare soil and the water characteristics of the field can provide information regarding the various soil types and the organic matter concentrations with the soil. Such data may be supplemented with physical soil testing. In addition to determining the microbial enzyme activity in the soil, a series of thermal images may be obtained of the field over the course of the growing season. For example, FIG. 5a contains the same visual spectrum and ADVI images as FIG. 4, and FIG. 5b contains two additional thermal images that were obtained later in the same growing season These images can indicate the temperature and moisture in the field over time. By analyzing the temperatures, moisture, and organic matter content of areas of the field, mineralization of these areas can be predicted using methods known to those knowledgeable in agricultural prescription techniques.

Because microbial enzymes within soil correlate to the rate and/or gross mineralization of nutrients such as nitrogen in the soil, the predicted microbial enzyme activity of each area of the field can be used to determine the area's ability to mineralize nitrogen and/or other nutrients. Nonlimiting methods for predicting mineralization rates in soil are disclosed in U.S. Pat. No. 6,699,709 to Bonde et al., incorporated herein by reference. An amount of naturally available nitrogen content in the soil may be determined based on the soil data and the determined mineralization rate of an area of the field. For example, as explained in U.S. Pat. No. 8,682, 584 to Baker et al., incorporated herein by reference, the total available nitrogen in a soil sample can be determined by summing he amounts of nitrate, ammonium, and mineralizable nitrogen in the sample.

An amount of nitrogen required by plants in a field may be based at least in part on predicted yield estimates for areas of the field, and this information may be used to designate biomass zones based on yield estimates. Aerial thermal, ADVI, and/or visual spectrum imagery of a field may be performed to identify biomass zones within the field based on plant growth factors, nonlimiting examples including plant population, vigor, accumulated stress, disease, and variety. If the field requires nitrogen to be applied to the field prior to planting crops (for example, if a late season nitrogen application method is not available for applying fertilizer to a field via a high clearance device), yield estimates for each biomass zone of the field may be based on intended plant population, variety, and planting date coupled with yield history and other agronomic factors (collectively referred to as intended and historic factors). Otherwise, if nitrogen is to be applied to the field after planting a crop, yield estimates may be predicted based on recorded growth factors of that crop in the field.

Figure 6A:
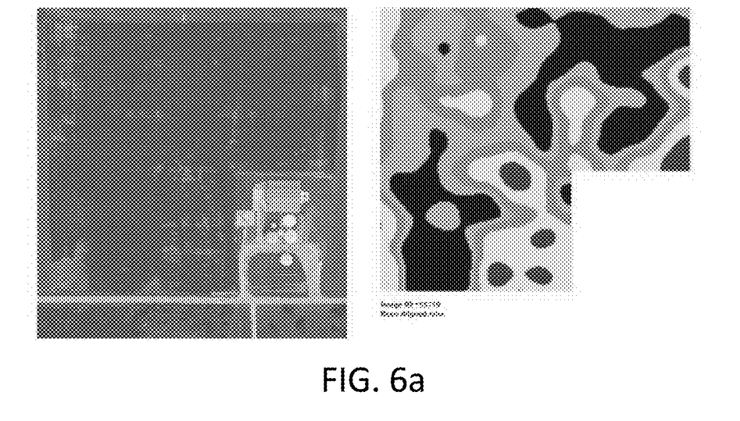
FIGS. 6a, 6b, and 6c contain three pairs of aerial visual spectrum and ADVI images of the field seen in FIG. 1 during different growing seasons of crops in the field.
Figure 6B:
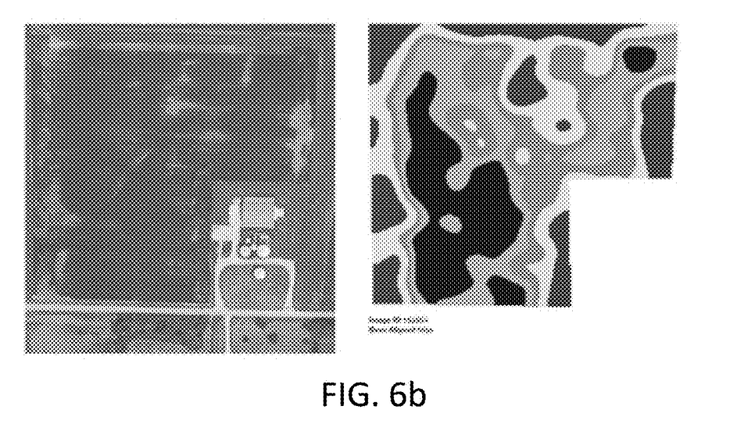
Figure 6C:
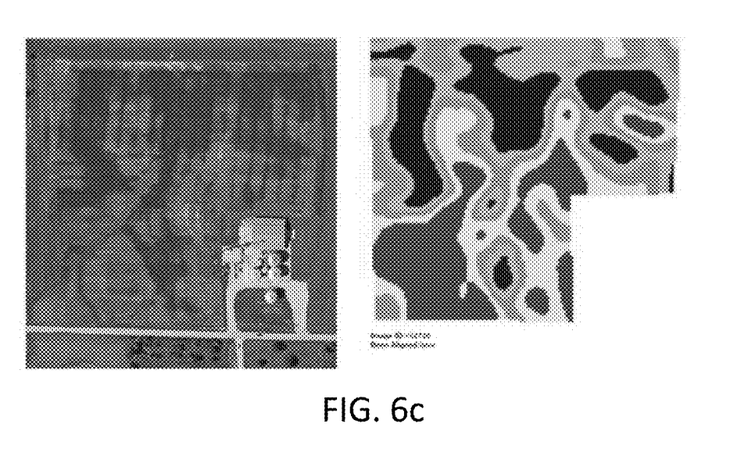
Figure 7:
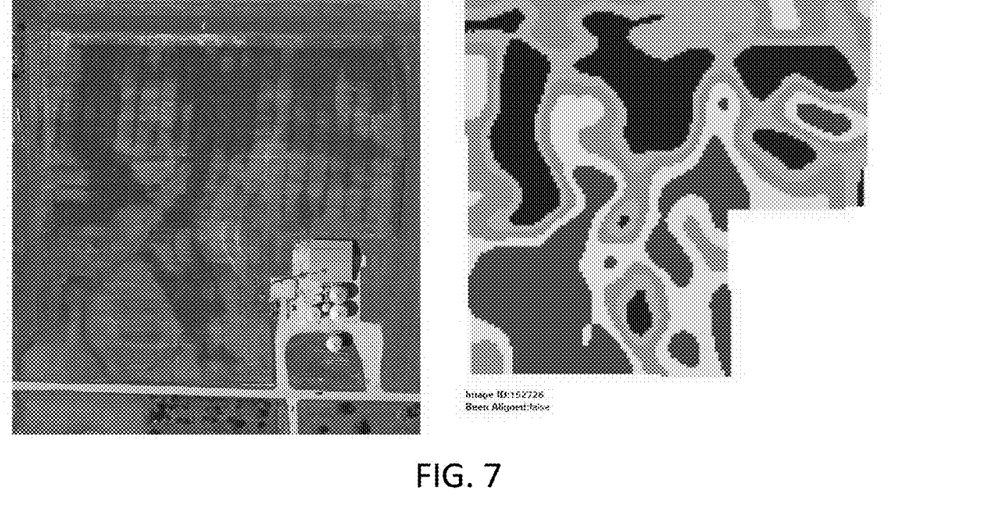
FIG. 7 contains the pair of aerial visual spectrum and ADVI images of FIG. 6c, in which high and low yield areas of the field have been identified for the crops growing in the field at that time.

Preferably, yield estimates are determined at least in part based on growth factors of the crops in the field that are determined using thermal systems and methods as disclosed in Sutton. Briefly, aerial thermal and visual spectrum images of plants growing in the field may be monitored to determine plant population, vigor, accumulated stress, disease, variety, weather factors, and the like over time during the growth of the plants. This collected data may be used to predict yield potential of each biomass zone. As a nonlimiting example, an aerial thermal image may be obtained of the field, and pixels corresponding to the coolest detected temperature, the warmest detected temperature, and an intermediate temperature therebetween may be identified. A farmer may then physically perform yield checks at the locations in the field corresponding to the three identified pixels on the thermal image having the coolest, warmest, and intermediate temperatures. Subsequently, the physical yield check data may be compared to the rest of the pixels in the thermal image to obtain a yield prediction of the entire field. The predicted yield potential (e.g., in bushels per acre based on intended and historic factors and/or recorded growth factors) for each biomass zone may be multiplied by a proprietary or industry recommended factor (e.g., 1.1 for corn) to determine an amount of nitrogen required for the plants in the field. FIGS. 6a, 6b, and 6c contain pairs of visual spectrum and ADVI images of the same field as shown in FIGS. 1a through 5b, but taken after crop emergence during different growing seasons (years) to evidence that optimal fertilization rates will vary from year to year. FIG. 7 contains a magnified image of FIG. 6c, and identifies a more lush (green) area of the field that will likely have higher yields and therefore have higher nitrogen requirements, and another area of the field that will likely have lower yields and therefore have lower nitrogen requirements.

All collected data may compiled to compare the collected data and determine properties of the various zones. For example, soil, water, and/or biomass zone maps or data may be overlaid and compared to determine water properties, yield estimates, and available/required nitrogen for each soil zone, to determine soil properties, water properties, and available nitrogen of each biomass zone, and/or to determine soil properties, yield potentials, and available/required nitrogen for each water zone. Furthermore, soil, water, and/or biomass zone maps or data may be overlaid or combined to produce a composite map designating crop management zones within the field having determined soil properties, water properties, and yield estimates (for example, nitrogen requirements).

Figure 8:
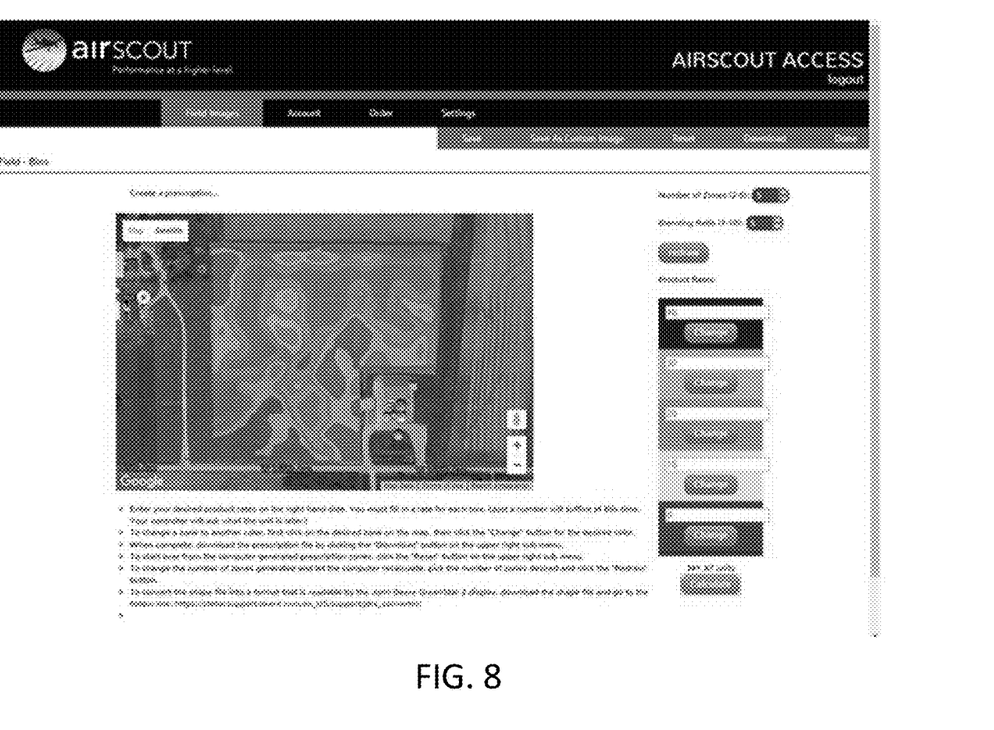
FIG. 8 contains a captured screen shot representing a nutrient prescription building tool indicating nitrogen rates to be applied in different zones of the field of FIG. 1 in accordance with a nonlimiting aspect of the invention.

Once a map has been produced that identifies individual zones having determined soil and water properties, yield estimates, and required nitrogen amounts, a nitrogen-containing fertilization prescription may be produced identifying amounts of fertilizer recommended for each individual zone of the field. For example, when using a composite map designating crop management zones, the naturally available nitrogen for each zone may be subtracted from the required nitrogen to determine amounts of nitrogen that must be applied to each crop management zone in the field to meet the needs of the plants growing in the respective zones. In the instance where the field is part of a farm, the calculated amount of nitrogen is the minimum amount that needs to be supplemented by a farmer to meet the requirements of the crops in the field with the intension of maximizing or achieving a desired yield. Nitrogen-containing fertilization prescriptions may be based on this amount to limit over fertilization of the field and thereby reduce costs to the farmer while also reducing damage to the surrounding environment from the over-application of fertilizer. It is foreseeable that the farmer may fertilize the crops more than once per growing season. In such instances, the above-noted calculations may further take into account amounts of nitrogen that have already been artificially applied to each crop management zone in the field. FIG. 8 represents a nonlimiting example of an operative prescription building tool that indicates on the righthand side of the screen what nitrogen rates should be applied in each crop management zone represented by a different color in the image of the field generated on the left-hand side of the screen. The resulting variable prescriptions may be uploaded to an application machine of any type available now or developed in the future in order to apply the recommended amounts of fertilizer.

The above methods improve on existing methods of producing agricultural prescriptions by providing an understanding of water and how it infiltrates the soil in a field, which is believed to affect many soil properties. For example, water is one of the most important factors in determining yearly crop growth, health, and yield. Despite this, hydrology of a field is commonly ignored or underrepresented in conventional methods of determining crop management zones within a field. For example, it is believed that simply analyzing rainfall rates and slope of the field are insufficient to effectively model a field and accurately produce nutrient prescriptions. Aerial thermal imaging may be used to significantly and practically improve measurements of water infiltration and an understanding of hydrology of soil. For example, each time a rain event occurs, it provides an opportunity to observe how the field handles the event. Depending on the previous condition of the soil, the rain intensity, field slope, the volume of water, etc., the field may react differently at each event (e.g., water movement and absorption may differ). With the knowledge gained from each event through aerial thermal imaging, models of the field may be further refined to determine nitrogen required verses nitrogen available. Therefore, a series of aerial thermal images obtained over a period of time during which numerous rain events have occurred can be analyzed to produce prescriptions with improved accuracy.

It is believed that the above methods cannot be accomplished by analyzing a single aerial thermal image, but rather requires analyzing a series of thermal images obtained over a period of time (e.g., a portion of a growing season), for example, following rain events by hours, days, and weeks, to determine how individual areas of a field react to water. By knowing this information, the corresponding areas of the field can be properly modeled to determine nitrogen mineralization and/or to improve the placement of probes or testing locations.

While the invention has been described in terms of specific or particular embodiments, it should be apparent that alternatives could be adopted by one skilled in the art. For example, the systems and their components could differ from the embodiments described herein, and method steps may be completed with various systems and processes. Accordingly, it should be understood that the invention is not necessarily limited to any embodiment described herein. It should also be understood that the phraseology and terminology employed above are for the purpose of describing the disclosed embodiments, and do not necessarily serve as limitations to the scope of the invention. Therefore, the scope of the invention is to be limited only by the following claims.

The invention claimed is:

1. A method comprising:
obtaining and recording a series of aerial thermal images and a series of aerial visual spectrum images of a field at different times over a period of time during a growing season of a crop growing in the field, at least first and second aerial thermal images of the series of aerial thermal images and at least first and second aerial visual spectrum images of the series of aerial visual spectrum images being obtained at first and second stages of the growing season, respectively; and
analyzing and comparing the first aerial thermal image and the first aerial visual spectrum image and analyzing and comparing the second aerial thermal image and the second aerial visual spectrum image to perform at least one of:
  determine nitrogen mineralization rates for the field;
  monitor water infiltration rates and soil hydrology of the field by obtaining the series of aerial thermal images and the series of aerial visual spectrum images prior to, during, and after rain events;
  determine location placement of soil probes to determine nitrogen mineralization in the field, uptake of nitrogen by plants in the field, available nitrogen in the field, and nitrogen required by the plants during growth; and
  determine locations for soil testing to determine nitrogen mineralization in the field, uptake of nitrogen by plants in the field, available nitrogen in the field, and nitrogen required by the plants during growth.

2. The method of claim 1, wherein the series of aerial thermal images and the series of aerial visual spectrum images are analyzed to determine the nitrogen mineralization rates for the field.

3. The method of claim 1, wherein the series of aerial thermal images and the series of aerial visual spectrum images are analyzed to also monitor the water infiltration rates and the soil hydrology of the field following rain events.

4. The method of claim 1, wherein the series of aerial thermal images and the series of aerial visual spectrum images are analyzed to also determine the location placement of the soil probes or the locations for soil testing.

5. The method of claim 1, further comprising recording moisture and temperature data with moisture and temperature probes in the field over the period of time, wherein the series of aerial thermal images and the series of aerial visual spectrum images are analyzed in combination with the moisture and temperature data to determine the nitrogen mineralization rates for the field.

6. The method of claim 5, further comprising analyzing the series of aerial thermal images and the series of aerial visual spectrum images to determine location placement for the moisture and temperature probes.

7. The method of claim 1, further comprising:
analyzing the aerial thermal images and the aerial visual spectrum images to predict a yield estimate for the field;
determining a total amount of nitrogen required by the plants in the field during the growing season based on the yield estimate; and then
producing a nitrogen-containing fertilization prescription by at least subtracting the amount of nitrogen naturally provided to the field via nitrogen mineralization from the total amount of nitrogen required by the plants.

8. The method of claim 1, wherein the series of aerial thermal images and the series of aerial visual spectrum images are analyzed to monitor the water infiltration rates and the soil hydrology of the field following rain events.

9. The method of claim 1, wherein the series of aerial thermal images and the series of aerial visual spectrum images are analyzed to determine the location placement of the soil probes to determine the nitrogen mineralization in the field, uptake of nitrogen by plants in the field, available nitrogen in the field, and nitrogen required by the plants during growth.

10. The method of claim 1, wherein the series of aerial thermal images and the series of aerial visual spectrum images are analyzed to determine the locations for the soil testing to determine the nitrogen mineralization in the field, uptake of nitrogen by plants in the field, available nitrogen in the field, and nitrogen required by the plants during growth.

11. The method of claim 1, wherein the field comprises bare soil having substantially no vegetation.

12. The method of claim 1, wherein the series of aerial visual spectrum images are indicative of light reflected by organic matter within the field and capture light in the near-infrared, visual, and ultraviolet spectrums, and the series of aerial thermal images are compared to the series of aerial visual spectrum images to compensate for moisture.

13. A system configured to perform the method of claim 1, the system comprising thermal and visual camera systems installed in an airplane that obtain the series of aerial thermal images and the series of aerial visual spectrum images, respectively.

14. A system configured to perform the method of claim 8, the system comprising thermal and visual camera systems installed in an airplane that obtain the series of aerial thermal images and the series of aerial visual spectrum images, respectively.

15. A system configured to perform the method of claim 9, the system comprising thermal and visual camera systems installed in an airplane that obtain the series of aerial thermal images and the series of aerial visual spectrum images, respectively.

16. A system configured to perform the method of claim 10, the system comprising thermal and visual camera systems installed in an airplane that obtain the series of aerial thermal images and the series of aerial visual spectrum images, respectively.

17. The method of claim 1, wherein the analyzing and comparing step determines the nitrogen mineralization rates for the field.

18. The method of claim 1, wherein the analyzing and comparing step monitors the water infiltration rates and soil hydrology of the field by obtaining the series of aerial thermal images and the series of aerial visual spectrum images prior to, during, and after rain events.

19. The method of claim 1, wherein the analyzing and comparing step determines the location placement of the soil probes to determine nitrogen mineralization in the field, uptake of nitrogen by plants in the field, available nitrogen in the field, and nitrogen required by the plants during growth.

20. The method of claim 1, wherein the analyzing and comparing step determines the locations for soil testing to determine nitrogen mineralization in the field, uptake of nitrogen by plants in the field, available nitrogen in the field, and nitrogen required by the plants during growth.

\* \* \* \* \*